United States Patent [19]

Beaty et al.

[11] Patent Number: 4,511,651

[45] Date of Patent: Apr. 16, 1985

[54] REAGENT COMPOSITION AND ASSAY FOR THE DETERMINATION OF γ-GLUTAMYLTRANSFERASE ACTIVITY

[75] Inventors: Larry E. Beaty, Indianapolis; Steven M. Lanham, Brownsburg, both of Ind.

[73] Assignee: American Monitor Corporation, Indianapolis, Ind.

[21] Appl. No.: 403,680

[22] Filed: Jul. 30, 1982

[51] Int. Cl.[3] .......................... C12Q 1/48; C12Q 1/36; C12N 9/96
[52] U.S. Cl. ........................................ 435/15; 435/24; 435/188; 435/810
[58] Field of Search ...................... 435/15, 23, 24, 188, 435/193, 810

[56] References Cited

U.S. PATENT DOCUMENTS

| | | | |
|---|---|---|---|
| 3,703,441 | 11/1972 | Nakanishi et al. | 435/24 |
| 3,769,173 | 10/1973 | Carroll | 435/24 |
| 3,773,626 | 11/1973 | Bernt et al. | 435/24 |
| 3,878,048 | 4/1975 | Carroll | 435/24 |
| 3,892,631 | 7/1975 | Carroll | 435/24 |
| 3,979,447 | 9/1976 | Bernt et al. | 435/15 |
| 4,087,331 | 5/1978 | Bucolo et al. | 435/15 |
| 4,372,874 | 2/1983 | Modrovich | 435/23 |
| 4,451,563 | 5/1984 | Kaufman | 435/23 |

FOREIGN PATENT DOCUMENTS

| | | | |
|---|---|---|---|
| 18628 | 11/1980 | European Pat. Off. | 435/15 |
| 170198 | 10/1982 | Japan | 435/15 |
| WO82/01564 | 5/1982 | PCT Int'l Appl. | 435/15 |

OTHER PUBLICATIONS

Kawaji et al., J. Clin. Chem. Clin. Biochem., 19(8): 727 (Aug. 1981).

*Primary Examiner*—Esther M. Kepplinger
*Attorney, Agent, or Firm*—Marilyn L. Amick

[57] ABSTRACT

An improved diagnostic assay and stabilized reagent composition for the determination of γ-glutamyltransferase activity in biological specimens using a buffered solution of γ-glutamyl-p-nitroanilide and glycylglycine, wherein β-cyclodextrin and preferably also dimethylsulfoxide have been added thereto.

4 Claims, No Drawings

REAGENT COMPOSITION AND ASSAY FOR THE DETERMINATION OF γ-GLUTAMYLTRANSFERASE ACTIVITY

BACKGROUND OF THE INVENTION

1. Field of the Invention

This invention relates to a novel reagent composition and its use in an assay for the determination of γ-glutamyltransferase activity in serum and other biological samples.

2. Nature and Usefulness of γ-Glutamyltransferase Determinations

Determinations of the quantity of the enzyme γ-glutamyltransferase, in human serum, are being performed in the clinical laboratory with ever increasing frequency. Such determinations appear to be the most sensitive screening test for liver disease currently available, since, almost without exception, a normal level of γ-glutamyltransferase denotes a healthy liver. The measurement of γ-glutamyltransferase is extremely useful to the physician in determining the extent of liver damage caused by chronic alcoholism, and in monitoring the progress of viral hepatitis. Levels of γ-glutamyltransferase are also increased in acute pancreatitis, in certain cardiovascular diseases, and in kidney failure; therefore, although the enzyme γ-glutamyltransferase has been known only since 1950, and it was not until the late 1960's that the development of new methodology for γ-glutamyltransferase determination permitted its full significance as a valuable diagnostic tool to become recognized and accepted, its determination is a most valuable part of any clinical testing profile. Correspondingly, the ease and other factors of the assays for this significant enzyme have been increasingly a matter of concern to the large and active field of diagnostic biomedical assays.

3. Description of the Prior Art

While the prior art has specified several methods in its search of assays to determine γ-glutamyltransferase activity, the methods generally considered suitable for use in the clinical laboratory have been those which use a synthetic γ-glutamyl substrate with chromogenic properties; for it is known that the enzyme γ-glutamyltransferase catalyzes the transpeptidation or transfer of γ-glutamyl groups from γ-glutamyl peptide substrates to suitable acceptors.

However, some of these substrates require the analyst to perform cumbersome and time-consuming procedural steps, and some of these substrates are considered to be carcinogenic substances and are therefore extremely dangerous for use by laboratory personnel. The method which utilizes γ-glutamyl-p-nitroanilide as the substrate and glycylglycine as the acceptor is therefore generally considered to be the safest and most practical of the various γ-glutamyltransferase assay methods, and may be described by the following reaction sequence:

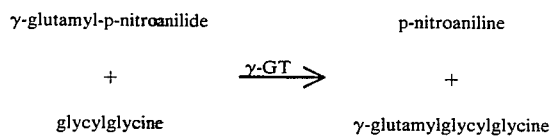

Unfortunately, however, there are two serious disadvantages hindering the routine and frequent use of this otherwise acceptable method, namely, the instability and poor solubility of the γ-glutamyl-p-nitroanilide substrate. It is not only difficult to dissolve the compound, but once solvation has been accomplished, the resulting solution remains usable for only a short period of time, usually no longer than two or three hours due to decomposition of the γ-glutamyl-p-nitroanilide. This problem is further exacerbated by the fact that any attempt to prolong stability by refrigeration of the solution will cause the substrate to crystallize and precipitate out of solution. It has generally been necessary to use temperatures as high as 50° to 60° C. in order to dissolve γ-glutamyl-p-nitroanilide; however, such temperatures are very close to that at which γ-glutamyl-p-nitroanilide will spontaneously hydrolyze, which obviously has a deleterious effect on the usefulness of the solution.

Carroll, in U.S. Pat. Nos. 3,769,173 (Oct. 30, 1973), 3,878,048 (Apr. 15, 1975), and 3,892,631 (July 1, 1975) describes a substrate composition wherein, in addition to the γ-glutamyl-p-nitroanilide and glycylglycine, there is also included sodium nitrite, an ammedial buffer, and, optionally, magnesium chloride hexahydrate. Carroll suggests that the magnesium chloride may help to keep the substrate in solution, but this was the extent of his teaching with regard to stabilizing γ-glutamyl-p-nitroanilide. Carroll's assay method, however, required three working reagents and several procedural steps, and thus would be considered too cumbersome and time-consuming to meet the needs of today's clinical laboratory and its need for high-volume and automated testing capabilities.

Bernt et al. in U.S. Pat. No. 3,979,447 (Sept. 7, 1976) and in U.S. Pat. No. 3,986,931 (Oct. 19, 1976) describe certain γ-glutamyl-p-nitroanilide compounds characterized by an acid group substituted at position 3 of the nitroaniline, which are claimed to help overcome the problems of instability and poor solubility. The preferred substrates of the Bernt et al. art are specified to be γ-glutamyl-3-carboxy-p-nitroanilide and γ-glutamyl-3-sulfo-p-nitroanilide. Indeed, these compounds do exhibit improved solubility characteristics and tend to precipitate out of solution less easily than the unsubstituted compound, and in this respect, stability is therefore improved.

However, the Bernt et al. art, other than asserting that the "stability is good", does not even venture to suggest any particular duration of stability; and it seems justified to presume that there still remained some drawbacks, at least with regard to stability, since in their teachings as to how to perform an assay, Bernt et al. chose to keep the substrate solution separate from the buffer solution and use two reagent pipetting steps to perform an assay. Furthermore, the preferred substrates of Bernt et al. have been found to exhibit diminished sensitivity when compared to that seen with unsubstituted γ-glutamyl-p-nitroanilide.

Nakanishi et al. in U.S. Pat. No. 3,703,441 (Nov. 21, 1972) attempted to improve the solubility and stability of γ-glutamyl-p-nitroanilide by including a combination of a particular surface active agent and a particular buffer. In their teachings, even a solution as strong as 30 percent dimethylsulfoxide was dismissed as being unsuitable as a solvent. Quite unexpectedly, therefore, it was found that as little as 1 percent dimethylsulfoxide was significantly effective in enhancing the stability of a solution containing γ-glutamyl-p-nitroanilide and β-cyclodextrin, especially at refrigerated storage temperatures.

SUMMARY OF THE INVENTION

Accordingly, the disadvantages of various prior art methods continuing to burden assays for this diagnostically significant enzyme, it is a general object of the present invention to provide a novel reagent composition and assay method for the determination of γ-glutamyl-transferase activity in blood serum. A more particular object is to provide a reagent composition utilizing the substrate γ-glutamyl-p-nitroanilide which requires no heating to prepare, and which nevertheless has improved stability. A further object is to provide an assay method which requires only a single working reagent, which is sensitive, and which provides an extended dynamic or linear range over which useful results may be obtained. These and other objects, features and achievements of the present invention will become apparent to those skilled in the art in the light of the teachings herein set forth.

It has been discovered that when γ-glutamyl-p-nitroanilide is introduced into a buffered solution containing β-cyclodextrin, there quite unexpectedly is formed a solution from which it is difficult to crystallize or precipitate γ-glutamyl-p-nitroanilide, even at refrigerated temperatures. These results are particularly surprising because benzene, phenolic, and aromatic moieties are known to form complexes with β-cyclodextrin and to precipitate out of solution. Moreover, when dimethylsulfoxide (DMSO) is also included in the solution, even greater solubility and stability of the solution is achieved.

The present invention, accordingly, comprises a novel reagent composition for the determination of γ-glutamyl-transferase in serum or other fluids. The reagent is comprised of a buffered solution of γ-glutamyl-p-nitroanilide, glycylglycine, dimethylsulfoxide, and β-cyclodextrin. Amounts of β-cyclodextrin between 1 and 19 grams per liter of reagent have been found to provide improved solubility of γ-glutamyl-p-nitroanilide at substrate concentrations customarily used in assays for γ-glutamyltransferase in biological fluids. Similarly, amounts of DMSO between 0.5 and 10 percent have been found to be useful in the practice of the present invention.

In addition to β-cyclodextrin, other useful cyclodextrins have been found to include those substituted with from 1 to 4 amino groups. The preferred buffer is 2-amino-2-methyl-1,3-propanediol (AMPD); however, any buffer known to be useful in assays for γ-glutamyltransferase may be used with the present invention. Optionally, the reagent may also have added thereto antimicrobial agents known to retard growth of microorganisms should accidental contamination occur.

Compositions prepared according to the concepts of the present invention may be stored at refrigerated temperatures without precipitate formation, and have been found to retain their utility for up to three weeks or longer. At lower refrigerated temperatures of about 0°–4° C., the dimethylsulfoxide is especially beneficial in preventing the co-precipitation of the β-cyclodextrin and the γ-glutamyl-p-nitroanilide. Further, when dimethylsulfoxide is preferably included, it helps in solubilizing endogenous serum lipoproteins and minimizing the effects of turbidity which might otherwise interfere in the assay. Although the compound glycylglycine is the currently preferred acceptor by those skilled in the art, it is not beyond the scope of the present invention to use others.

For performing γ-glutamyltransferase determinations, the pH of the reagent solution should ideally be about pH 8.4 to assure optimal substrate conversion by the enzyme. Minor variations from this pH, however, may be made to meet certain specific requirements or needs without departing from the inventive concepts.

To use the reagent composition of the present invention to perform an assay for γ-glutamyltransferase, a sample of serum or other fluid is combined with the reagent composition under controlled conditions of temperature and time. The rate of formation of the yellow-colored p-nitroaniline compound cleaved by the enzyme from the substrate is a measure of the γ-glutamyltransferase activity present in the sample. The formation of the yellow compound may be measured photometrically at approximately 405 nm. Using the reagent composition of the preferred embodiments described herein, the dynamic range, or linearity of the assay, has been enhanced and extended beyond that of prior art methods. Depending upon the particular reaction conditions of temperature, time, and sample to reagent volume ratio, useful results are obtained at γ-glutamyltransferase levels of 500 units/liter and greater.

DESCRIPTION OF THE PREFERRED EMBODIMENTS

The specific embodiments of the present invention detailed herein are provided to enable an analyst skilled in the art to understand and produce reagents and to perform an assay according to the novel concepts and achievements of the present invention.

EXAMPLE 1

Reagent Preparation

A diagnostic reagent is prepared by first dissolving about 1.3 grams γ-glutamyl-p-nitroanilide in 100 milliliters of 0.25N hydrochloric acid. This first solution is then added to one liter of a second solution which has been prepared as follows:

12.8 grams 2-amino-2-methyl-1,3-propanediol, 5.8 grams sodium chloride, 8.12 grams glycylglycine, and 11.1 grams β-cyclodextrin are combined with about 800 ml deionized water and brought to pH 8.6 using hydrochloric acid. Fifty milliliters dimethylsulfoxide are then added and the final volume brought to 1 liter with deionized water.

The pH of the final solution will be about 8.2–8.4 and may be adjusted if desired to fit specific assay requirements.

In an alternative embodiment, the γ-glutamyl-p-nitroanilide, the 0.25N hydrochloric acid, and the second solution may be prepared and dispensed into three separate containers wherein prolonged storage of a year or more is desired. This method of preparation is especially desirable when manufacturing diagnostic kits wherein maximum stability of the pre-formulated reagents is especially important. Prior to performing an assay, the analyst merely dissolves the γ-glutamyl-p-nitroanilide in the dilute HCl and then adds this first solution to the already prepared second solution.

The diagnostic reagent prepared as described above will retain its usefulness for several weeks or longer if stored under refrigeration (about 4°–8° C.). To guard against accidental contamination such as might happen in a busy laboratory, antimicrobial or preservative agents known to those skilled in the art may also be added to the reagent. Care should be taken that any preservatives so added do not inhibit the assay reaction.

EXAMPLE 2

Determination of γ-Glutamyltransferase

To perform an assay for γ-glutamyltransferase, 200 microliters of the sample to be assayed are added to 3.0 milliliters of the reagent which has been pre-warmed to 37° C. Following incubation at 37° C. for one minute, absorbance readings at 405 nm are made at timed intervals, from which the average change in absorbance per minute is then determined ($\Delta A_{405}$/min). This $\Delta A_{405}$/min is then compared to the $\Delta A_{405}$/min obtained when a standard calibration material containing a known quantity of γ-glutamyltransferase is similarly treated.

To calculate the γ-glutamyltransferase activity of the sample, divide the $\Delta A$/min of the sample by the $\Delta A$/min of the calibrator, and then multiply the result thus obtained by the known amount of γ-glutamyltransferase in the calibrator. Alternatively, one may omit the assay of a calibrator and calculate the amount of γ-glutamyltransferase in the sample based on the extinction coefficient at 405 nm of p-nitroaniline using the mathematical formula well-known to those skilled in the art of performing enzyme assays.

The present invention is conveniently and advantageously practiced using laboratory instrumentation, i.e. analyzers, capable of automatically sampling specimens, dispensing reagents, and measuring absorbance with precise exactness of timing. An example of such an instrument is the KDA (Reg. TM) analyzer manufactured by American Monitor Corporation, Indianapolis, Ind., which has been used in carrying out a preferred embodiment of the present invention. When using the KDA analyzer, 100 microliters of sample and 1.3 milliliters of reagent were used, and the rate of formation of the yellow p-nitroaniline was measured at 410 nm.

Photometric measurement of the rate of formation of the colored reaction product is desirably made at about 405 nm. Where instrumentation is used employing bichromatic measurements, two appropriate wavelengths may be utilized. For example, when the ABA-100 (ABA is a registered trademark of Abbott Laboratories, Chicago, Ill.) bichromatic analyzer was used, the readings were made at 415 nm and 450 nm. (The sample and reagent volumes used were 5 and 250 microliters, respectively.) Further, it is not considered beyond the scope of the present invention to make photometric measurements using reflectance techniques rather than absorbance techniques.

Other modifications and alterations to the foregoing embodiments will be apparent to those skilled in the art and are not to be considered beyond the scope of the novel concepts of the present invention.

What is claimed is:

1. A reagent composition for the determination of the enzyme γ-glutamyltransferase in a fluid, comprised of:
   (a) an enzymatically reactive amount of γ-glutamyl-p-nitroanilide;
   (b) a buffer;
   (c) a glycylglycine; and
   (d) a cyclodextrin from the group consisting of β-cyclodextrin and cyclodextrins substituted with 1 to 4 amino groups in an amount between about 1 and 19 grams per liter.

2. A reagent composition as recited in claim 1, further comprising dimethylsulfoxide in an amount between about 0.5 and 10 percent.

3. A method for the determination of the enzyme γ-glutamyltransferase in a fluid, comprising the steps of:
   (a) combining a sample of said fluid with a reagent to form a reaction mixture, said reagent comprising:
      (i) an enzymatically reactive amount of γ-glutamyl-p-nitroanilide,
      (ii) a buffer,
      (iii) glycylglycine, and
      (iv) a cyclodextrin from the group consisting of β-cyclodextrin and cyclodextrins substituted with 1 to 4 amino groups in an amount between about 1 and 19 grams per liter; and
   (b) measuring the change in absorbance of said reaction mixture.

4. A method as recited in claim 3, said reagent further comprising dimethylsulfoxide in an amount between about 0.5 and 10 percent.

* * * * *